US011896268B2

(12) United States Patent
Linares

(10) Patent No.: US 11,896,268 B2
(45) Date of Patent: Feb. 13, 2024

(54) EXPANDABLE SPINAL RACK GEAR JACK FOR INSTALLATION BETWEEN UPPER AND LOWER SUCCEEDING SUPERIOR ARTICULAR PROCESSES

(71) Applicant: Linares Spinal Devices, LLC, Auburn Hills, MI (US)

(72) Inventor: Miguel A. Linares, Bloomfield Hills, MI (US)

(73) Assignee: Linares Spinal Devices, LLC, Auburn Hills, MI (US)

( * ) Notice: Subject to any disclaimer, the term of this patent is extended or adjusted under 35 U.S.C. 154(b) by 0 days.

(21) Appl. No.: 18/073,750

(22) Filed: Dec. 2, 2022

(65) Prior Publication Data

US 2023/0233332 A1 Jul. 27, 2023

Related U.S. Application Data

(60) Provisional application No. 63/302,179, filed on Jan. 24, 2022.

(51) Int. Cl.
*A61B 17/70* (2006.01)
*A61F 2/44* (2006.01)
*A61F 2/30* (2006.01)

(52) U.S. Cl.
CPC ...... *A61B 17/7065* (2013.01); *A61B 17/7062* (2013.01); *A61F 2/4405* (2013.01); *A61F 2002/30329* (2013.01)

(58) Field of Classification Search
CPC ............ A61B 17/7062; A61B 17/7065; A61B 17/7067; A61B 17/7068
See application file for complete search history.

(56) References Cited

U.S. PATENT DOCUMENTS

| 8,545,563 | B2 | 10/2013 | Brun et al. | |
|---|---|---|---|---|
| 8,585,738 | B2 | 11/2013 | Linares | |
| 8,623,056 | B2 | 1/2014 | Linares | |
| 9,023,108 | B2 | 5/2015 | Hansell et al. | |
| 9,237,954 | B2 * | 1/2016 | Butler | A61F 2/44 |
| 11,432,937 | B1 * | 9/2022 | Linares | A61F 2/30749 |
| 2006/0004447 | A1 * | 1/2006 | Mastrorio | A61B 17/7065 623/17.11 |
| 2007/0100340 | A1 * | 5/2007 | Lange | A61B 17/7065 606/279 |
| 2008/0114456 | A1 * | 5/2008 | Dewey | A61B 17/7065 623/17.16 |
| 2008/0234824 | A1 * | 9/2008 | Youssef | A61B 17/7062 623/17.11 |
| 2010/0106190 | A1 * | 4/2010 | Linares | A61B 17/7067 606/249 |

(Continued)

*Primary Examiner* — Julianna N Harvey
*Assistant Examiner* — Holly Joanna Lane
(74) *Attorney, Agent, or Firm* — Dinsmore & Shohl LLP

(57) ABSTRACT

A spinal jack adapted for installation between first and second vertebral processes, including a three dimensional and arcuate ergonomic main body constructed from first and second subset body portions, from which is displaceable an upper body between retracted and expanded positions. Each of the jack halves further includes gripping portions adapted for engaging the vertebral processes. A geared mechanism is provided for expanding or retracting the jack halves in order to establish a corrected adjusted orientation between the processes.

6 Claims, 4 Drawing Sheets

(56) References Cited

U.S. PATENT DOCUMENTS

| | | | |
|---|---|---|---|
| 2012/0323276 A1* | 12/2012 | Okamoto | A61B 17/7065 606/249 |
| 2013/0184751 A1* | 7/2013 | Siegfried | A61B 17/7068 606/279 |
| 2021/0052307 A1 | 2/2021 | Soo et al. | |
| 2023/0136415 A1* | 5/2023 | Linares | A61B 17/7062 606/247 |

* cited by examiner

EXPANDABLE SPINAL RACK GEAR JACK FOR INSTALLATION BETWEEN UPPER AND LOWER SUCCEEDING SUPERIOR ARTICULAR PROCESSES

CROSS REFERENCE TO RELATED APPLICATIONS

The present application claims the priority of U.S. Ser. No. 63/302,179 filed Jan. 24, 2022.

FIELD OF THE INVENTION

The present invention relates generally to spinal jacks for providing inter-vertebral support. More specifically, the present invention teaches an adjustable spinal jack for installation between superior articular processes of upper and lower succeeding vertebrae.

BACKGROUND OF THE INVENTION

Spinal jacks designs are known in the prior art for providing adjusted and secure positioning support between succeeding spinal vertebra. Examples of these are depicted in each of Linares U.S. Pat. No. 8,623,056 and Linares U.S. Pat. No. 8,585,738.

SUMMARY OF THE PRESENT INVENTION

The present invention discloses a spinal jack adapted for installation between first and second vertebral processes, including a three dimensional and arcuate ergonomic main body constructed from first and second subset body portions, from which is displaceable an upper body between retracted and expanded positions. Each of the jack halves further includes gripping portions adapted for engaging the vertebral processes. A geared mechanism is provided for expanding or retracting the jack halves in order to establish a corrected adjusted orientation between the processes.

Additional features include the upper body further having a pair of downwardly extending stems which are anchored at upper ends to lateral extending lips of the upper body, the stems extending downwardly and respectively seating within and through elongated interior channels defined in each of extending sides of the second and upper positioned subset body portion. The geared mechanism further includes a tool bit engageable drive gear and inter-engaging driven gear, the gears each engaging linearly teethed ends of the stems for displacing the stems and the upper body relative to the main body.

Other features include body and inter-expandable jack halves further including any medical grade metal or plastic. The gripping portions each further include spaced apart sides and an interconnected recessed end defining a pocket adapted to receive the vertebral process therebetween. The pockets each further include textured surfaces for providing additional gripping of the vertebral processes.

Each of the subset portions of said the body further include an opposing base within which is configured a recessed cavity for receiving the gears. Additional cavities are configured into the main body for seating said displaceable stems. An aperture in the main body is adapted to receiving therethrough the tool bit. The drive gear further includes a bit receiving location not limited to a hex key profile.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses an adjustable spinal jack for installation between superior articular processes of upper and lower succeeding vertebrae. A general representation of a selected jack is depicted generally at 10 in a retracted position in FIG. 1, and is further shown in each of succeeding FIGS. 2-3 positioned between upper 2 and lower 4 successive superior articular processes corresponding to upper and lower vertebrae.

The present invention provides an expandable spinal jack which overcomes many of the disadvantages of the prior art and provides an effective solution for stabilizing and fixing in position a given orientation established between the succeeding vertebrae. As will be further described, the spinal jack designs described herein further permit adjustment, at any future time following initial surgical implantation, in a minimally invasive fashion and in order to re-adjust the spatial positioning established between the upper and lower separable halves or sections, such as in order to compensate and correct for future/downstream vertebral complications following the initial implantation of the spinal jack.

Figure 1:
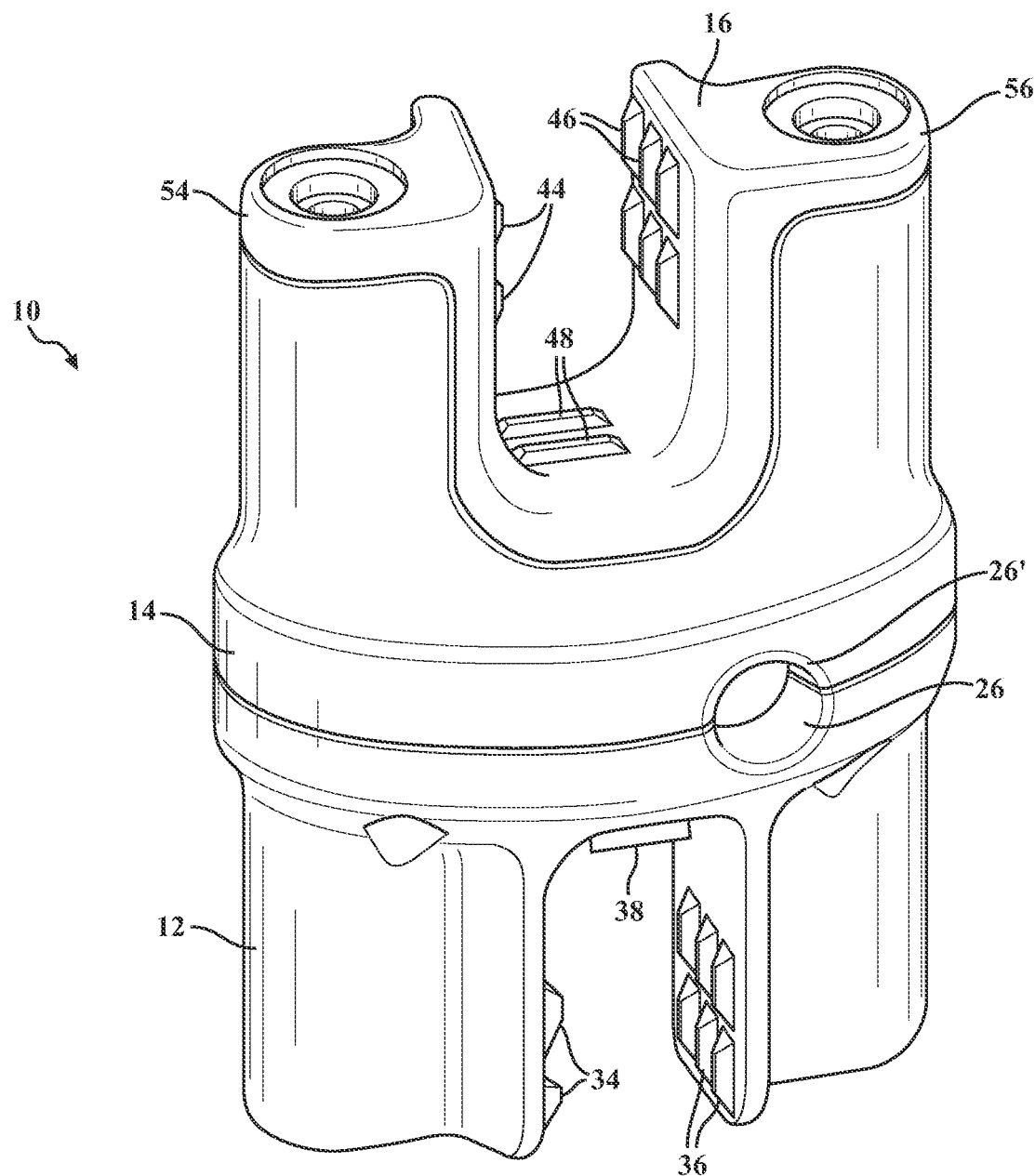
FIG. 1 is a perspective view of a spinal jack according to the present invention.
Figure 3:
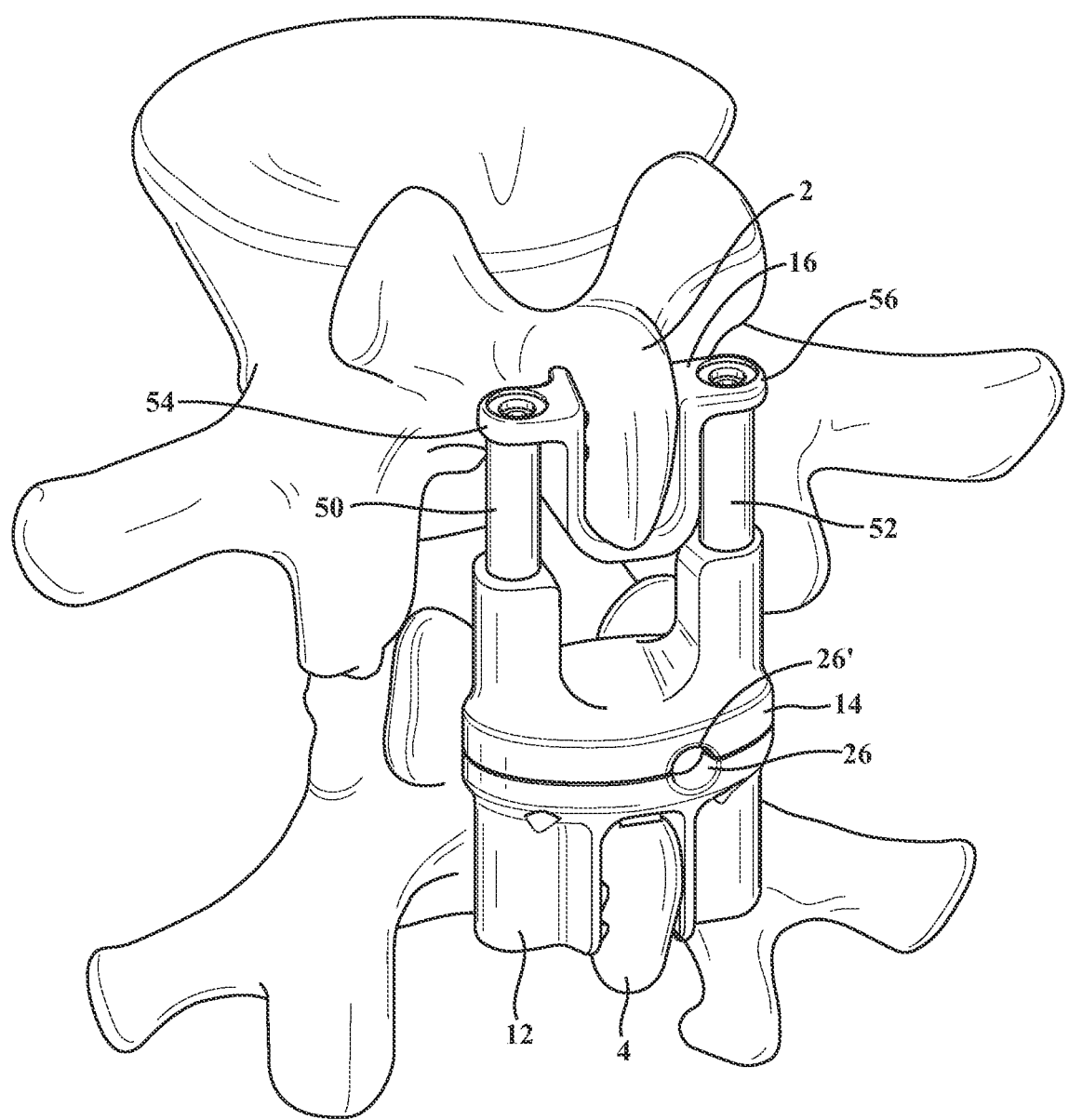
FIG. 3 is a succeeding view to FIG. 2 and depicting the spinal jack in an expanded position for properly orienting the vertebrae.

Proceeding to FIG. 1, an environmental illustration is generally shown of the spinal jack 10 substantially as shown in FIG. 1 in a retracted position. In combination with the expanded position of FIG. 3, the spinal jack includes a three dimensional and arcuate ergonomic main body, this constructed from first 12 and second 14 subset body portions, from which is displaceable an upper body 16 (as best shown in FIG. 3). The main body 12/14 and upper displace-able body 16 are each constructed of a suitable sanitary medical grade material not limited to any of a metal or plastic composition.

Figure 4:
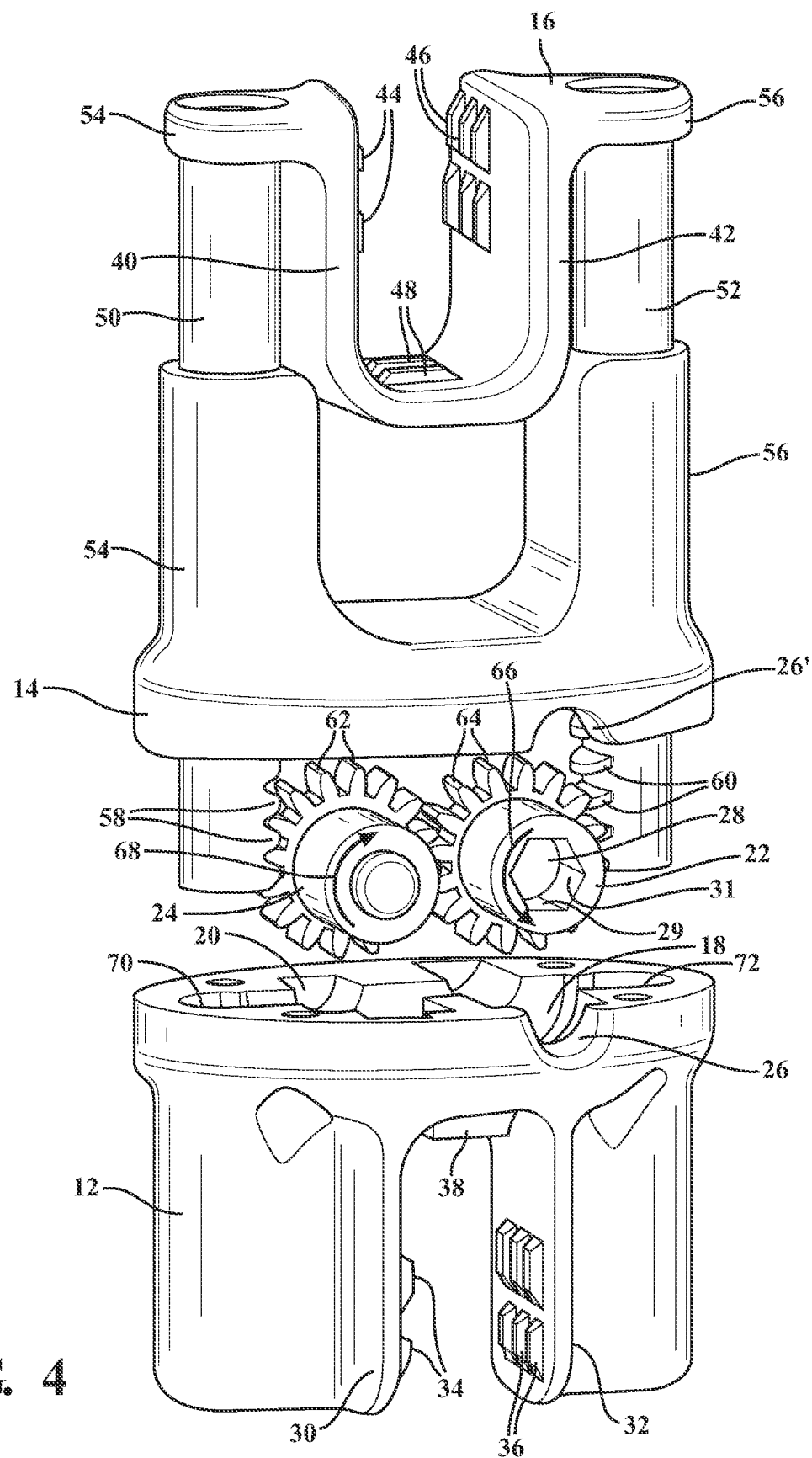
FIG. 4 is an exploded view of the spinal jack assembly and depicting the interior gearing for separating the upper and lower halves.

Each of the main body subset portions 12 and 14 depict a substantial "U" shape, with a base of each being arranged in a mirrored opposing and abutting end face orientation. An interior recessed cavity is formed within each opposing base (as shown in FIG. 4 including locations 18 and 20 associated with subset body portion 12), these collectively seating a pair of meshing drive 22 and driven 24 gears in a side-by-side configuration.

An inlet aperture to the drive gear 22 is provided by subset rim portions 26 and 26' (see FIG. 4) which align between the opposing end faces of the subset body portions 12/14. In this fashion, a receiving aperture is formed within which a tool bit or the like (not shown) can be inserted into engagement with a central bit receiving location 28 for actuating the drive gear 22 and meshing driven gear 24. The present invention contemplates any bit configuration for rotating the drive gear 22, such including without limitation a hex key profile as depicted by interconnected sides 29, 31, et seq. in FIG. 4.

Each of the subset body portions 12/14 also depict inwardly contoured or recessed channels for receiving the superior articular processes 2 and 4. A first lower channel is configured in the lower positioned the subset body portion 12 and is defined by a pair spaced apart extending sides 30/32, each further exhibiting opposing side surface gripping locations 34/36 and a further inside middle gripping location 38 for configuring a first process receiving pocket.

As shown, the upper body 16 includes an upper recessed channel defined by a further pair of spaced apart sides 40/42, each further exhibiting opposing side surface gripping locations 44/46 and a further inside middle gripping location 48 for configuring a second process receiving pocket. The spaced apart pairs of sides 30/32 and 40/42 of the opposite extending gripping portions are adapted to seat the upper 2 and lower 4 consecutive superior articular processes, the inner "U" shaped surface profile of each of the gripping portions is further exhibited by any type of textured or ribbed profile, the purpose of which is to provide additional resistive engagement against the facet surfaces of the processes 2 and 4.

Although not shown, any type of screw fastener can be employed with each gripping portion and which, upon positioning the gripping portions and drilling through the processes 2 and 4, provides for anchoring the lower and upper jack halves to the respective vertebrae. Alternatively, the gripping portions are crimped into engagement with the vertebral processes 2 and 4, such as without the use of separate screws.

As best shown in FIGS. 3-4, the upper body 16 includes a pair of elongated stems 50 and 52 which are anchored at upper ends to lateral outermost extending lips 54 and 56 of the upper body 16. The stems 50/52 extend downwardly and respectively seat within and through elongated interior channels or passageways defined in each of extending sides 54 and 56 of the upper positioned of the main body subset portion 14.

Figure 2:
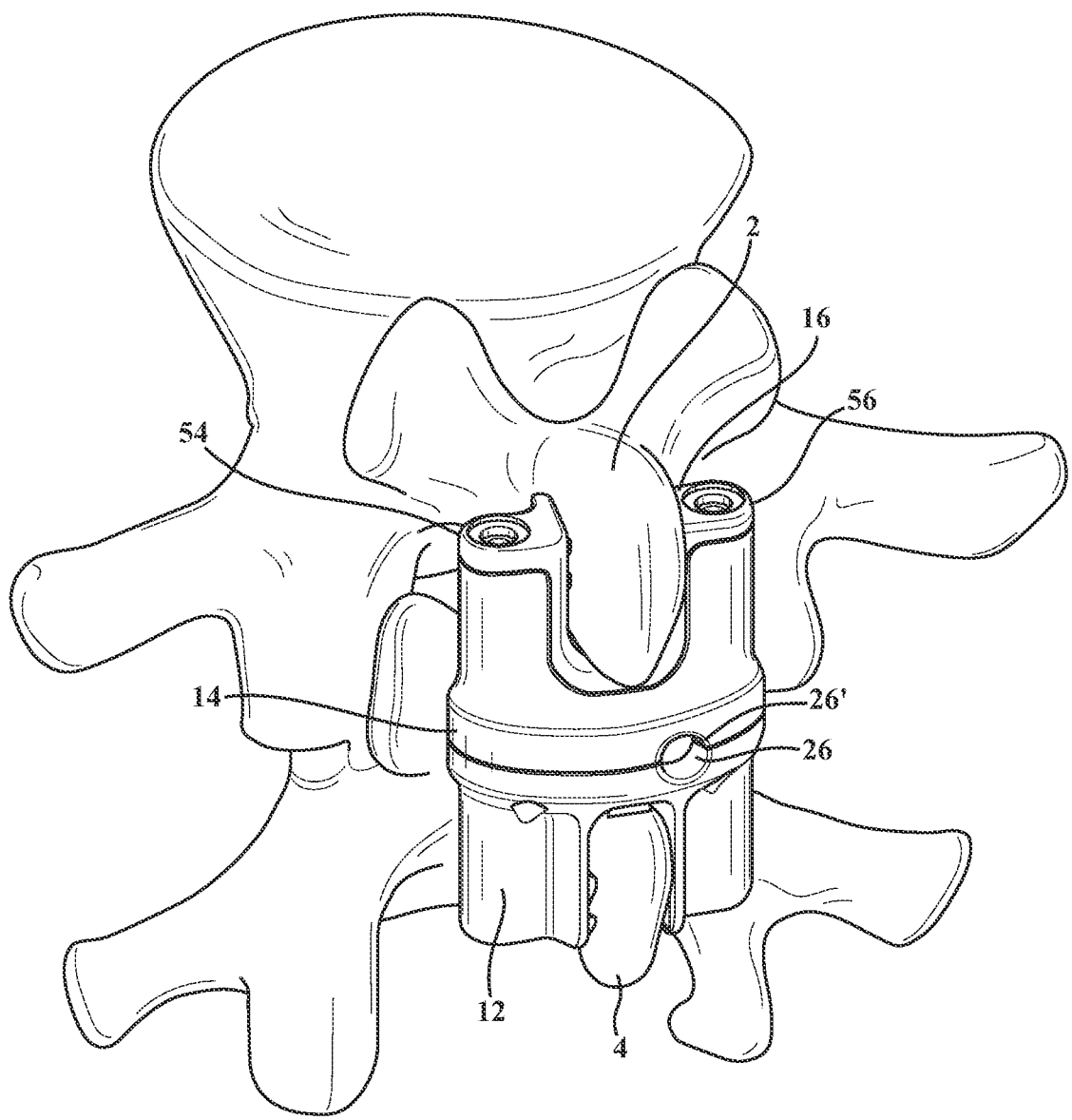
FIG. 2 is an environmental illustration of a spinal jack of FIG. 1 depicted in a retracted position installed between succeeding superior articular processes associated with upper and lower consecutive spinal vertebrae.

As again shown in FIG. 4, bottom extending portions of each stem 50/52 further exhibit inward facing teethed or serrated portions (at 58 and 60) which are linearly arrayed and which interface with the exterior teeth (at 62 and 64) of the driven 24 and drive 22 gears. In this fashion, and upon pre-positioning and initial attachment of the spinal jack 10 between the succeeding superior articular processes as best shown in FIG. 2, the tool bit is inserted through the collectively defined aperture (26/26') and into the bit receiving recess 28 of the drive gear 22 and further, upon being rotated in a selected counter-clockwise direction (see arrow 66 in FIG. 4), results in the driven gear 22 being counter-rotated in a clockwise direction (see arrow 68) in order to synchronously actuate the stems 50/52 and to relatively displace (extend or retract) the upper and lower jack halves.

In this manner, the stems 50/52 are elevated along with the upper supported and process engaging body 16 relative to the assembled subset portions 12/14 of the lower main body. As again best shown in FIG. 4, additional recesses/cavities are defined in exposed end faces of the lower body portions 12/14 (see at 70 and 72 for lower body portion 12) for seating the extending displaceable ends of the stems 50/52 in a manner allowing for a degree of bi-directional adjustment of the upper spinal jack half 16 relative to the inter-assembled lower spinal jack half 12/14.

Although not shown, it is envisioned and understood that any type of biasing spring can be incorporated into the jack body for influencing the spaced stems 50/52 of the upper body 16 in either of an extensible or retracting position relative to the lower main body, and which assists in maintaining a desired spatial positioning of the jack halves between the processes 2 and 4, such as in order to alleviate patient pain/discomfort resulting for vertebral misalignments. As further understood, additional spinal braces and the like can be provided (not shown) which can be installed against the later processes of each vertebrae and in order to provide additional vertebral support depending upon the nature of the spinal injury being addressed.

Having described my invention, other and additional preferred embodiments will become apparent to those skilled in the art to which it pertains, and without deviating from the scope of the appended claims. The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly.

Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A spinal jack adapted for installation between first and second vertebral processes, comprising:
   a main body constructed from first and second assembled subset body portions;
   an upper body supported upon said main body and displaceable relative to said main body between retracted and expanded positions;
   said upper body further including a pair of downwardly extending stems seating within interior channels defined in said main body;
   each of said main and upper bodies further including gripping portions adapted for engaging the vertebral processes; and
   a geared mechanism seated within opposing arcuate shaped cavities formed in said first and second subset body portions, said arcuate shaped cavities extending from opposing end faces of said subset body portions which align upon assembly for receiving and rotatably supporting each of a tool bit engageable drive gear and an inter-engaging driven gear, said interior channels within said main body for seating said downwardly extending stems communicating with said arcuate shaped cavity formed in said first body portion, said gears each engaging linearly teethed ends of said stems for displacing said stems and said upper body relative to said main body to adjust an orientation between the processes, an inlet aperture to said drive gear further including opposing and semi-circular shaped rim portions configured within said subset body portions which align between opposing end faces of said subset body portions such that, upon assembly, said rim portions define a circular passageway for communicating the tool bit with the drive gear.

2. The spinal jack of claim 1, said bodies further comprising any medical grade metal or plastic.

3. The spinal jack of claim 1, said gripping portions each further comprising a "U" shaped configuration including spaced apart sides and an interconnected recessed end defining a pocket adapted to receive the vertebral process therebetween.

4. The spinal jack of claim 3, said pockets each further including textured surfaces adapted for providing additional gripping of the vertebral processes.

5. The spinal jack of claim 1, said drive gear further comprising a bit receiving location not limited to a hex key profile.

6. The spinal jack of claim 1, said upper body further comprising lateral outermost lips for supporting said downwardly extending stems.

* * * * *